(12) United States Patent
Pikul et al.

(10) Patent No.: US 6,548,539 B1
(45) Date of Patent: Apr. 15, 2003

(54) AGENTS FOR REGULATION OF COLON CANCER GENE EXPRESSION

(75) Inventors: Stanislaw Pikul, Germantown, MD (US); Daniel R. Soppet, Centreville, VA (US); Paul E. Young, Gaithersburg, MD (US)

(73) Assignee: Avalon Pharmaceuticals, Gaithersburg, MD (US)

( * ) Notice: Subject to any disclaimer, the term of this patent is extended or adjusted under 35 U.S.C. 154(b) by 0 days.

(21) Appl. No.: 10/090,866

(22) Filed: Mar. 5, 2002

Related U.S. Application Data (60) Provisional application No. 60/273,467, filed on Mar. 5, 2001.

(51) Int. Cl.$^7$ .................. A61K 31/34; A61K 31/17; A61K 31/165; C07D 301/02; C07C 273/00
(52) U.S. Cl. .................. 514/473; 514/596; 514/617; 549/475; 564/48; 564/184; 564/186
(58) Field of Search .................. 549/475; 564/48, 564/184, 186; 514/473, 596, 617

(56) References Cited

U.S. PATENT DOCUMENTS

| | | | |
|---|---|---|---|
| 6,225,329 B1 * | 5/2001 | Richter et al. | 514/359 |
| 6,342,521 B1 * | 1/2002 | Reiter | 514/472 |
| 6,344,476 B1 * | 2/2002 | Ranges et al. | 514/447 |
| 6,413,947 B1 * | 7/2002 | Shiraishi et al. | 514/110 |

\* cited by examiner

*Primary Examiner*—Deborah C. Lambkin
(74) *Attorney, Agent, or Firm*—Elliott M. Olstein; Alan J. Grant (57) ABSTRACT

Compounds of the general structure according to Formula (I)

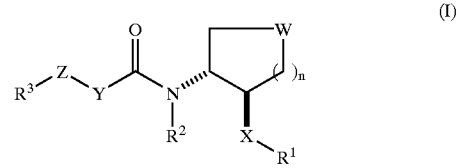

wherein $R^1$ is selected from alkyl, alkenyl, alkynyl, heteroalkyl, haloalkyl, aryl, arylalkyl, heteroaryl, heteroarylalkyl, cycloalkyl, and heterocycloalkyl; $R^2$ is selected from alkyl, alkenyl, alkyny, heteroalkyl, haloalkyl, arylalkyl, heteroarylalkyl, cycloalkylalkyl, and heterocycloalkylalkyl; $R^3$ is selected from aryl, heteroaryl, cycloalkyl, and heterocycloalkyl; W is selected from $Ch_2$, O and S; n is 0 to about 3: X is selected from S or O; Y, if present, is selected from a bond, aryl, NH, NR, O or S, where $R^3$ is selected from hydrogen, alkyl, alkenyl, alkynyl, heteroalkyl, haloalkyl, arylalkyl, heteroarylalkyl, cycloalkylalkyl, and heterocycloalkylalkyl; and Z, if present, can represent a bond or is selected from lower alkyl, O or S are disclosed. Also disclosed are uses of such compounds for treating a variety of disease conditions, including cancer.

16 Claims, 2 Drawing Sheets

AGENTS FOR REGULATION OF COLON CANCER GENE EXPRESSION

This application claims the benefit of U.S. Provisional Application No. 60/273,467, filed Mar. 5, 2001, the disclosure of which is hereby incorporated by reference in its entirety.

FIELD OF THE INVENTION

The present invention relates to chemical agents affecting levels of gene expression in cellular systems, especially cancer cells.

BACKGROUND OF THE INVENTION

Screening assays for novel drugs are based on the response of model cell based systems in vitro to treatment with specific compounds. Various measures of cellular response have been utilized, including the release of cytokines, alterations in cell surface markers, activation of specific enzymes, as well as alterations in ion flux and/or pH. Some such screens rely on specific genes, such as oncogenes (or gene mutations).

BRIEF SUMMARY OF THE INVENTION

In one aspect, the present invention relates to novel organic compounds, most with aromatic rings, that have the ability to function as gene modulators for genes found in cancer cells and which genes are found to be up regulated or down regulated in cancer cells, especially colon cancer cells.

In one embodiment of the present invention, the compounds disclosed herein are able to up regulate genes found to be up regulated in normal (i.e., non-cancerous) cells versus cancer cells, especially colon cancer cells, thereby producing an expression profile for said gene(s) that more resembles the expression profile found in normal cells. In another embodiment, the compounds disclosed herein are found to down regulate genes found to be up regulated in cancer cells, especially colon cancer cells, relative to normal (i.e., non-cancerous) cells thereby producing an expression profile for said gene(s) that more resembles the expression profile found in normal cells. Thus, in addition to activity in modulating a particular gene that may or may not have a major role in inducing or sustaining a cancerous condition, the agents disclosed herein also find value in regulating a set of gene whose combined activity is related to a disease condition, such as cancer, especially colon cancer, including adenocarcinoma of the colon. Thus, while an overall set of genes is modulated, the effect of modulating any subset of these may be disproportionately large or small with respect to the effect in ameliorating the overall disease process. Consequently, different disease conditions may rely on different subsets of genes to be active or inactive as a basis for the overall disease process.

Thus, the present invention relates to novel organic compounds that have the ability to function as gene modulators for genes found in normal (i.e., non-cancer) cells and which genes are found to be up regulated or down regulated in normal cells, especially colon cells. Such an effect may prevent a disease condition, such as cancer, from arising in those otherwise more susceptible to such a condition. In one such embodiment, administration of one or more of the agents disclosed herein may succeed in preventing a cancerous condition from arising.

In other embodiments, the agents disclosed herein find use in combination with each other as well as with other agents, such as where a mixture of one or more of the agents of the present invention are given in combination or where one or more of the agents disclosed herein is given together with some other already known therapeutic agent, possibly as a means of potentiating the affects of such known therapeutic agent or vice versa.

The present invention also relates to processes of preventing or treating disease conditions, especially cancer, most especially colon cancer, by administering to a subject, such as a mammal, especially a human, a therapeutically active amount of one or more of the agents disclosed herein, including where such agents are given in combination with one or more known therapeutic agents.

BRIEF DESCRIPTION OF THE DRAWINGS

FIG. 1 (panels 1A and 1B) shows the structures of the compounds identified in Table 1. The identification numbers in the figure match those listed in the "compound" column of Table 1.

DETAILED DESCRIPTION OF THE INVENTION

The present invention relates to antitumor agents capable of modulating the expression of specified genes, or sets of genes, found to be active, or possibly inactive or functioning at a low degree of expression, relative to normal cells.

In particular, the compounds are found to affect expression of genes from a colon cancer signature set. Expression levels of such genes are markedly altered in cells derived from human colon cancer tissue as compared to cells derived from healthy individuals. Because the compounds disclosed herein can affect gene expression they may be useful for the treatment of many types of cancers, particularly colon cancer. Additionally, the compounds may be useful for the treatment of a variety of other conditions associated with changes in levels of gene expression.

The ability of compounds described herein to affect gene expression is a novel observation, and such activity could not be predicted based on information available in the public domain. Compounds with this activity may have the ability to affect the cell cycle of the transformed cells (cancer cells) and selectively induce them back into a normal state or into apoptosis (cell death). Therefore, the compounds may have a significant therapeutic potential for the treatment of cancer and other conditions associated with changes in levels of gene expression.

In accordance with the present invention, the compounds disclosed herein have been shown to modulate gene expression using a model cellular systems employing the HT29 colon tumor cell line (used for the data reported in Table 1). In such assays, primary cells, or tissue samples, are maintained in growth medium and are treated with compounds at a single concentration (10 $\mu$M for the data of Table 1) or at a range of concentrations (such as from 1 $\mu$M up to 100 $\mu$M). At specific times after treatment at the given concentration of test compound, cellular RNAs are isolated from the treated cells, primary cells or tumors, which RNAs are indicative of expression of selected genes, including, but not limited to, the genes used herein. The cellular RNA is then divided and subjected to analysis that detects the presence and/or quantity of specific RNA transcripts, which transcripts may then be amplified for detection purposes using standard methodologies, such as, for example, reverse transcriptase polymerase chain reaction (RT-PCR), etc. The presence or absence, or levels, of specific RNA transcripts are determined from these measurements and a metric derived for the type and degree of response of the sample to the treated compound compared to control samples. One such procedure is shown in example 8 where test compound may or may not be present.

The characteristic genes, or signature sets of genes and gene sequences whose expression is modulated by the agents disclosed herein are ones that are linked to, or used to characterize, the cancerous, or non-cancerous, status of the cells, or tissues, to be tested. They may also be linked to other diseases as disclosed herein. Thus, the compounds disclosed herein include novel anti-neoplastic agents that effect alteration of expression of small sets of characteristic, or indicator, or signature genes in specific model systems. In accordance with the present invention, analogs of such compounds are routinely produced by combinatorial methods and then readily assayed with a variety of cell lines or with primary samples from tumors maintained in vitro under suitable culture conditions for varying periods of time, or in situ in suitable animal models.

For example, Gene 2 was a gene that encodes a kallikrein. Tissue or glandular kallikreins are members of a large and highly conserved family of serine proteases that are central to many physiological processes. They are secreted protein-cleaving enzymes that process for example kininogen (local blood flow, sodium balance, inflammation, cell proliferation), growth factors (EGF, NGF, vasoactive peptide), or other substrates. The prostate antigens hK2 and PSA are members of this family. Diseases in which kallikreins have been implicated include acute pancreatitis, inflammatory arthritis and inflammatory bowel disease, sepsis, enterocolitis, arterial and salt-sensitive hypertension, blood coagulation disorders, scorpion and snake envenomation, infections and cancer. Thus, the chemical agents disclosed herein find use in the treatment and/or prevention of any of these diseases.

The genes utilized for the set of genes modulated by the compounds disclosed herein are also related to other disorders, such as cardiovascular disorders, arthritis, osteoporosis, inflammation and skin disorders. Cardiovascular disorders may include dilated cardiomyopathy, congestive heart failure, atherosclerosis, plaque rupture, reperfusion injury, ischemia, chronic obstructive pulmonary disease, angioplasty restenosis, and aortic aneurysm. Thus, the chemical agents disclosed herein find use in the treatment and/or prevention of any of these diseases as well.

In accordance with the present invention, certain genes have been identified that are expressed at levels in cancer cells that are different than the expression levels in non-cancer cells. In one instance, the identified genes are expressed at higher levels in cancer cells than in normal cells. In another instance, the identified genes are expressed at lower levels in cancer cells as compared to normal cells.

In accordance with the foregoing, the therapeutic, including anti-neoplastic, agents disclosed herein are screened using a process comprising the steps of:

(a) exposing cells to a chemical agent to be tested for antineoplastic activity, and (b) determining a change in expression of at least one gene of interest, such as one of the genes used to accumulate the data of Table 1. In such assay, a change in expression is indicative of anti-neoplastic activity.

Thus, in determining the therapeutic ability of the agents disclosed herein, a set of 11 genes related to colon cancer cells were used to ascertain the ability of these agents to modulate activity of this gene set. Other gene sets related to other diseases, including other cancers, can likewise be conveniently used for such screenings.

In one embodiment of the present invention, the compounds disclosed herein are able to up regulate genes found to be up regulated in normal (i.e., non-cancerous) cells versus cancer cells, especially colon cancer cells, thereby producing an expression profile for said gene(s) that more resembles the expression profile found in normal cells.

In another embodiment, the compounds disclosed herein are found to down regulate genes found to be up regulated in cancer cells, especially colon cancer cells, relative to normal (i.e., non-cancerous) cells thereby producing an expression profile for said gene(s) that more resembles the expression profile found in normal cells. Thus, in addition to activity in modulating a particular gene that may or may not have a major role in inducing or sustaining a cancerous condition, the agents disclosed herein also find value in regulating a set of gene whose combined activity is related to a disease condition, such as cancer, especially colon cancer, including adenocarcinoma of the colon. Thus, while an overall set of genes is modulated, the effect of modulating any subset of these may be disproportionately large or small with respect to the effect in ameliorating the overall disease process. Consequently, different disease conditions may rely on different subsets of genes to be active or inactive as a basis for the overall disease process.

Thus, the present invention relates to novel organic compounds that have the ability to function as gene modulators for genes found in normal (i.e., non-cancer) cells and which genes are found to be up regulated or down regulated in normal cells, especially colon cells. Such an effect may prevent a disease condition, such as cancer, from arising in those otherwise more susceptible to such a condition. In one such embodiment, administration of one or more of the agents disclosed herein may succeed in preventing a cancerous condition from arising.

More particularly, the anti-neoplastic agents of the present invention were screened by exposing a known cancerous cell to one of the disclosed chemical agents and then allowing said chemical agent to modulate the activity of one or more genes present in said cell, herein one or more of the genes mentioned in Table 1, then determining the expression of one or more of said genes of step (b) and then comparing the expression of said genes in the presence or absence of exposure to chemical agent, wherein a difference in expression is indicative of anti-neoplastic activity.

In specific embodiments, a chemical agent of the present invention is found to modulate the expression of more than one said gene, especially where it modulates at least two said genes, more especially where at least 3, or at least 5 of said genes, or more of said genes in a signature set are modulated. In a preferred embodiment, all of said genes are modulated. Table 1 shows the ability of several of the compounds disclosed herein to modulate a large percentage of the 11 genes used as a signature set for colon cancer. Such modulation occurred to varying degrees and in only 2 of the seven cases were fewer than all 11 genes modulated, some upward and some downward.

In one embodiment of the present invention, said gene modulation is downward modulation, so that, as a result of exposure to the chemical agent to be tested, one or more genes of the cancerous cell will be expressed at a lower level (or not expressed at all) when exposed to the agent as compared to the expression when not exposed to the agent.

In a preferred embodiment a selected set of genes are expressed in the reference cancer cell, especially a colon cancer cell, but not expressed in a cancer cell, especially a colon cancer cell, in contact with the chemical agent. Thus, where said chemical agent causes the gene, or genes, of a cancer cell to be expressed at a lower level than the same genes of a cancer cell not contacted with the chemical agent, this downward modulation indicates anti-neoplastic activity.

In a separate embodiment, exposure of cancer cells to a chemical agent of the invention may result in upward modulation of said genes, interpreted as meaning that said genes are expressed where previously not expressed, or else are expressed in greater quantities when exposed to the agent as compared to non-exposure to the agent. Such upward modulation may be taken as indicative of anti-neoplastic activity by the chemical agent(s) where increased expression of the gene, or genes, results in decreased growth and/or increased differentiation of said cells away from the cancerous state. For example, in the data of Table 1, genes 3 and 11, both up-regulated by AV-97, are likewise expressed at a higher level in normal cells so that the result of contacting the cancer cells with this agent is to make such expression in the tumor cells more like that of normal cells. Such patterns of expression are useful with respect to other cancers as well. For example, a similar gene has been found to be down-regulated in advanced prostate cancer. [See: Garrett S H, Sens M A, Shukla D, Flores L, Somji S, Todd J H, Sens D A., Metallothionein isoform 1 and 2 gene expression in the human prostate: downregulation of MT-1X in advanced prostate cancer. Prostate 43(2):125–35 (2000)].

Genes whose modulation is effected by compounds disclosed according to the invention may also include mutated forms of genes involved in the disease state, especially wherein such mutations may, of course, be a causative factor in the under or over expression of such genes in cancer cells.

Relative antineoplastic activity of the compounds of the present invention, and structurally and functionally related compounds, depends partly on the extent to which a given chemical agent modulates the expression of genes present in a cancerous cell. Thus, a first chemical agent that modulates the expression of a gene associated with the cancerous state (i.e., a gene that includes one of the sequences disclosed herein and present in cancerous cells) to a larger degree than a second chemical agent is thereby deemed to have higher, or more desirable, or more advantageous, anti-neoplastic activity than said second chemical agent. Alternatively, where first and second chemical agents modulate expression of more than one of said genes, but where the second modulates expression of, for example, five said genes, whereas the first modulates expression of only three of said genes, especially where the three form a subset of the five, then the second chemical agent is deemed a more potent anti-neoplastic agent within the invention.

The activity of the compounds of the invention in modulating gene activity was determined using RNA expression as an indicator although this is not the only way of measuring such activity. Thus, the greater the level of RNA (messenger RNA) detected the higher the level of expression of the corresponding gene. Gene expression, either absolute or relative, such as where the expression of several different genes are being quantitatively evaluated and compared, for example, where chemical agents modulate the expression of more than one gene, such as a set of 3, 4, 5, or more genes, is determined by the relative expression of the RNAs encoded by such genes.

RNA may be isolated from samples in a variety of ways, including lysis and denaturation with a phenolic solution containing a chaotropic agent (e.g., triazol) followed by isopropanol precipitation, ethanol wash, and resuspension in aqueous solution; or lysis and denaturation followed by isolation on solid support, such as a Qiagen resin and reconstitution in aqueous solution; or lysis and denaturation in non-phenolic, aqueous solutions followed by enzymatic conversion of RNA to DNA template copies.

In measuring the anti-neoplastic activity of the compounds of the present invention, steady state RNA expression levels for the genes, and sets of genes, studied herein were obtained prior to assaying the compounds. It is the steady state level of such expression that is affected by potential anti-neoplastic agents. Such steady state levels of expression are easily determined by any methods that are sensitive, specific and accurate. Such methods include, but are in no way limited to, real time quantitative polymerase chain reaction (PCR), for example, using a Perkin-Elmer 7700 sequence detection system with gene specific primer probe combinations as designed using any of several commercially available software packages, such as Primer Express software., solid support based hybridization array technology using appropriate internal controls for quantitation, including filter, bead, or microchip based arrays, solid support based hybridization arrays using, for example, chemiluminescent, fluorescent, or electrochemical reaction based detection systems.

In specific embodiments of the present invention, the antineoplastic activity of a compound is manifested as its effect not just on a single gene but on the overall genetic pattern found for a cancerous cell or tissue. Here, the genetic pattern is the modulation of expression (either up-regulation or down-regulation) of more than one gene, and the advantage of using the agents disclosed herein may lie in their ability to modulate activity of one or more key genes or their ability to change the overall expression profile of a set of genes, such as the 11 genes utilized in demonstrating activity of the agents disclosed herein, and thereby altering the overall expression profile of these genes so as to produce a more normal profile.

The gene patterns indicative of a cancerous state need not be characteristic of every cell found to be cancerous. Thus, the compounds of the present invention may not have anti-neoplastic activity on all cancerous cells but only on a large subset of a population of cancerous cells. In such cases, the compounds of the present invention may be used in different combinations to produce an overall anti-neoplastic effect on a particular tissue or cancer cell type, such as colon cancer.

It should be noted that there are a variety of different contexts in which genes have been evaluated as being involved in the cancerous process. Thus, some genes may be oncogenes and encode proteins that are directly involved in the cancerous process and thereby promote the occurrence of cancer in an animal. In addition, other genes may serve to suppress the cancerous state in a given cell or cell type and thereby work against a cancerous condition forming in an animal. Other genes may be involved either directly or indirectly in the cancerous process or condition and may serve in an ancillary capacity with respect to the cancerous state. All such types of genes are deemed with those to be determined in accordance with the invention as disclosed herein. Thus, the agents disclosed herein may operate by down-regulating the activity of an oncogene as well as by up-regulating the activity of a tumor suppressor gene. In addition, the activity of a gene modulated by the agents disclosed herein may be genes whose action is to produce a transcription factor that itself modulates the activity of other genes involved in the cancerous process.

By way of example, Gene 2 has been implicated as having tumor suppressor activity in breast and prostate cancer [Goyal J, Smith K M, Cowan J M, Wazer D E, Lee S W, Band V., *Cancer Res.* 58(21):4782–6 (1998)]. Thus, up-regulation of this gene may have the ability to prevent cancer initiation and/or progression.

In accordance with the foregoing, the present invention relates to cancer modulating agents that are themselves small chemical entities that affect the cancerous process, either in vivo or ex vivo. Said cancer modulating agent may have the effect of increasing gene expression or said cancer modulating agent may have the effect of decreasing gene expression as such terms have been described herein.

In keeping with the disclosure herein, the present invention also relates to a process for preventing or treating cancer comprising contacting a cancerous cell with an agent having activity against an expression product encoded by a gene sequence related to the cancerous state. Thus, some or all of the genes within the set of genes used to collect the data of Table 1 represent individual targets for therapeutic intervention, based at least in part on their pattern(s) of expression.

Of course, nothing need be known about the endogenous ligands or binding partners for such cell surface molecules. Rather, the effect of a therapeutic agent as disclosed herein on the gene or protein involved in a disease process, such as the cancerous process, is all that is required. The therapeutic agents disclosed herein can thus, using the general assay procedures disclosed herein, be measured for their ability to act in treating other disease processes that are affected by genes whose activity is modulated by these compounds, which diseases can include a wide spectrum other than just cancer. Of course, in such cases, the genes to be tested are determined by the intent and goals of the user. The data disclosed herein merely provide one use of the disclosed compounds and in no way represents a limit on their therapeutic activity.

The process of the present invention includes embodiments of the above-recited process wherein said cancer cell is contacted in vivo as well as ex vivo, with an agent disclosed herein.

In other embodiments, the agents disclosed herein find use in combination with each other as well as with other agents, such as where a mixture of one or more of the agents of the present invention are given in combination or where one or more of the agents disclosed herein is given together with some other already known therapeutic agent, possibly as a means of potentiating the affects of such known therapeutic agent or vice versa.

The compounds of the invention have the general structure as follows:

$R^1$ = lower alkyl, heteroalkyl, arylalkyl, heteroarylalkyl, aryl, heteroaryl; preferably lower alkyl or aryl.
$R^2$ = lower alkyl, heteroalkyl, arylalkyl, heteroarylalkyl; preferably lower alkyl, heteroalkyl or arylalkyl.
$R^3$ = aryl, heteroaryl, cycloalkyl or heterocycloalkyl; preferably aryl or cycloalkyl.
W is selected from $CH_2$, O and S;
n = 0, 1, 2 or 3; preferably 1 or 2.
X = S, O; preferably S.
Y = bond, NH, NR, O, $CH_2$; preferably NH or $CH_2$ or may not be present
Z = bond, lower alkyl, O or S; preferably bond, lower alkyl or O or may not be present
Stereochemistry designations are relative and not absolute.

Methods well known in the art for making formulations are found in, for example, *Remington: The Science and Practice of Pharmacy*, (19th ed.) ed. A. R. Gennaro, 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

For use in an animal, preferably a mammal, most preferably a human being, such treatment will commonly require treatment at different doses that may have to be determined based on the age, sex, and other clinical conditions at presentment. Recommended dosages consequently depend on the sound judgment of the physician in charge but will commonly be within the range of about 0.1 milligrams to 1,000 milligrams per kilogram of body weight, preferably in the range of about 0.1 mg to about 100 mg per kg body weight and most preferably in the range of about 0.1 mg to about 10 mg per kg body weight. In one embodiment, the dosage is between 5 mg and 1 gram total per adult human being, preferably between 5 mg and 500 mg, most preferably between 5 mg and 100 mg per dose to an adult human. Such doses are considered sufficient for oral administration. Where the dose is to be administered intravenously, differences in the desired dosage may be required, with the dosage commonly being reduced versus the corresponding oral dosage. The proper adjustment for such dosage levels based on route of administration are left to the sound judgment of the clinician.

DEFINITIONS

The following is a list of definitions for terms used herein, especially in the Examples.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the accepted meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

Compound Preparation

The compounds of the invention can be prepared using a variety of procedures known in the art. The starting materials used in preparing the compounds of the invention are known, made by known methods, or are commercially available. Particularly preferred syntheses are described in the following general reaction schemes. The R groups used to illustrate the reaction schemes do not necessarily correlate to the respective R groups used to describe the Formula I compounds. That is, for example, $R^1$ in Formula (I) may be different from $R^1$ as depicted in the below schemes). Specific examples for making the compounds of the present invention are set forth and in Examples 1–7.

Scheme 1

In Scheme 1, the trans thiosulfide S1b, functionalized with various substituents $R^1$, is readily available from the corresponding olefin S1a using known methods described in literature (for example: Balescia, F. et. al., Synthetic Commun. 1992, 22, 1101; Gritsenko, E. I. et. al., Zh. Org. Khim. 1984, 20, 741, or Hopkins, P. B. et. al., J. Org. Chem. 1978, 43, 1208). Selected compounds of this type may also be commercially available, e.g. 1-chloro-2-methylthio-cyclopentane ($R^1$=Me and n=1). The chlorine atom in S1b can be replaced with retention of configuration by nitrogen-based nucleophiles including ammonia and various amines to provide unsubstituted ($R^2$=H) or N-substituted ($R^2$=alkyl, etc.) thioamine S1c, respectively. The newly introduced amine functionality of S1c can, in turn, be substituted using a wide variety of acylating agents (e.g. acid anhydrides, acid chlorides, isocyanates, etc.) using methods well known to the skilled artisan to introduce substituent $R^3$. This way the target molecule S1c is obtained following a concise synthetic scheme that allows for advantageous modification of all three substituents ($R^1$, $R^2$ and $R^3$).

Scheme 2

In Scheme 2, an unsubstituted thiamine S2b is prepared from the olefin S1a using known methodology developed by Gontcharov, A. V. et. al. (Organic Lett. 1999, 1, 783). The intermediate aziridine S2a can be reacted with a variety of sulfur-, nitrogen- or oxygen-based nucleophiles to introduce substituent $R^1$ and different heteroatom-based linkers (X=S, N or O, respectively). In order to introduce substituent $R^2$ compound S2b can be subjected to the reductive amination reaction using methods well known to the skilled artisan.

Finally, acylation of the amine S1c is carried out as described above to provide the target molecule S1d.

Scheme 3

In Scheme 3, an alternative approach is used starting from a readily available acylated aziridine S3a. Such aziridines have been shown to undergo Lewis acid catalyzed ring opening reactions when treated with variety of thiols to give the corresponding trans thioamides S3b. Asymmetric version of this reaction has also been developed using chiral dialkyl tartrate based catalyst (Hayashi, M. et. al., Tetrahedron 1996, 52, 7817). If necessary, amide S3b can be further modified by through the introduction of substituent $R^2$. This can be accomplished using standard acylation techniques under basic conditions.

These steps may be varied to increase yield of desired product. The skilled artisan will recognize the judicious choice of reactants, solvents, and temperatures is an important component in any successful synthesis. Determination of optimal conditions, etc. is routine. Thus, the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will recognize that some reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. Such reactions are well within the ability of the skilled artisan. Some examples are found in T. Greene, *Protecting Groups in Organic Synthesis*. Of course, amino acids used as starting materials with reactive side chains are preferably blocked to prevent undesired side reactions. The compounds of the invention may have one or more chiral centers and one can prepare a selected optical isomer, either the diastereomer or the enantiomer, by using chiral starting materials, catalysts, solvents, or reagents, including preparing the racemic mixture of these. Such racemic mixtures can, when necessary, be separated into chiral components by methods known in the art, including, but not limited to, the use of chiral salts, chiral chromatography and the like.

In addition, it is to be appreciated that one optical isomer may have favorable properties over the other and thus the disclosure of a racemic mixture within the present invention may also include either optically active isomer if physiologically active in accordance with the methods of the invention.

In carrying out the following synthetic procedures, it should be borne in mind that, typically, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

MeOH=methanol
EtOAc=ethylacetate
Ph=phenyl
DMF=N,N-dimethylformamide
DME=dimethoxyethane
conc=concentrated
DCC=1,3-Dicyclohexylcarbodiimide
HOBT=1-Hydroxybenzotriazole
$Et_3N$=triethylamine
$Et_2O$=diethylether
boc=t-butyloxycarbonyl
acac=acetyl acetate
dil=dilute
wrt=with respect to The R groups used to illustrate the compound examples do not correlate to the respective R groups used to describe the various moieties of Formula (I). That is, for example, $R^1$, $R^2$ and $R^3$ used to describe Formula (I) in the Summary of the Invention section and Section II of the Detailed Description do not represent the same moieties as $R_1$, $R_2$, and $R_3$ in this Section VIII.

EXAMPLES 1–4

The following chart shows the structure of compounds made according to the description in Examples 1–4 described below:

| Example | n | R¹ | R² |
|---|---|---|---|
| 1 | 1 | —CHMe₂ | —Ph |
| 2 | 1 | —CH₂CH₃ | —Ph |
| 3 | 1 | —CH₂OCH₃ | —CH₂OPh |
| 4 | 2 | —H | -cyclo-Bu |

The present invention will now be further described by way of the following non-limiting example. In applying the disclosure of the example, it should be kept clearly in mind that other and different embodiments of the methods disclosed according to the present invention will no doubt suggest themselves to those of skill in the relevant art.

Example 1

N-Isobutyl-N-(2-phenylsulfanyl-cyclopentyl)-benzamide a) (2-Chloro-cyclopentylsulfanyl)-benzene. Cyclopentene (3.40 g, 50 mmol) is added dropwise at room temperature to a solution of phenylsulfenyl chloride (7.2 g, 50 mmol) in DMSO (100 mL). The resulting mixture is stirred at 4° C. overnight and then the solvent is removed under reduced pressure. Saturated NaHCO₃ solution is added and the resulting mixture is extracted with EtOAc. The organic extracts are dried (Na₂SO₄) and then concentrated to an oil under reduced pressure. The crude material is purified by chromatography on silica gel (hexane/EtOAc) to provide the desired product.

b) Isobutyl-(2-phenylsulfanyl-cyclopentyl)-amine. To a solution of (2-chloro-cyclopentylsulfanyl)-benzene (387 mg, 2 mmol) in tetrahydrofuran (5 mL) is added triethylamine (200 mg, 2 mmol) and iso-butylamine (293 mg, 4 mmol). The resulting mixture is stirred at 100° C. for two hours, cooled and then the solvent is removed under reduced pressure. The residue is dissolved in ethyl acetate and the organic phase is washed with 5% aqueous NaHCO₃, brine, dried (Na₂SO₄) and then concentrated to an oil under reduced pressure. The crude product is used in the next step without further purification.

c) N-Isobutyl-N-(2-phenylsulfanyl-cyclopentyl)-benzamide. To a solution of isobutyl-(2-phenylsulfanyl-cyclopentyl)-amine (250 mg, 1 mmol) in dichloromethane (10 mL) is added triethylamine (200 mg, 2 mmol) and a crystal of 4-dimethylaminopyridine followed by benzoyl chloride (168 mg, 1.2 mmol). The resulting mixture is stirred at room temperature overnight and then the mixture is partitioned between ethyl acetate and 5% aqueous NaHCO₃. The organic phase is washed with brine, dried (Na₂SO₄) and then concentrated to an oil under reduced pressure. The crude material is purified by chromatography on silica gel (hexane/EtOAc) to provide the target product. MS: M+H⁺ 354.

Example 2

N-(2-Phenylsulfanyl-cyclopentyl)-N-propyl-benzamide

Example 2 is prepared according to the procedure described for Example 1 using n-propylamine in step 1b. MS: M+H⁺340.

Example 3

N-(2-Methoxy-ethyl)-2-phenoxy-N-(2-phenylsulfanyl-cyclopentyl)-acetamide a) (2-Methoxy-ethyl)-(2-phenylsulfanyl-cyclopentyl)-amine. To a solution of (2-chloro-cyclopentylsulfanyl)-benzene (387 mg, 2 mmol) in terahydrofurane (5 mL) is added triethylamine (200 mg, 2 mmol) and methoxyethylamine (300 mg, 4 mmol). The resulting mixture is stirred at 100° C. for two hours, cooled and then the mixture is partitioned between ethyl acetate and 5% aqueous NaHCO₃. The organic phase is washed with water and brine, dried (Na₂SO₄) and then concentrated to an oil under reduced pressure. The crude product is used in the next step without further purification.

b) N-(2-Methoxy-ethyl)-2-phenoxy-N-(2-phenylsulfanyl-cyclopentyl)-acetamide. To a solution of (2-methoxy-ethyl)-(2-phenylsulfanyl-cyclopentyl)-amine (251 mg, 1 mmol) in dichloromethane (10 mL) is added triethylamine (200 mg, 2 mmol) and a crystal of 4-dimethylaminopyridine followed by phenoxyacetyl chloride (205 mg, 1.2 mmol). The resulting mixture is stirred at room temperature overnight and then the mixture is partitioned between ethyl acetate and 5% aqueous NaHCO₃. The organic phase is washed with brine, dried (Na₂SO₄) and then concentrated to an oil under reduced pressure. The crude material is purified by chromatography on silica gel (hexane/EtOAc) to provide the target product. MS: M+H⁺386.

Example 4

Cyclobutanecarboxylic acid methyl-(2-phenylsulfanyl-cyclohexyl)-amide

Example 4 is prepared according to the procedure described for Example 1 using cyclohexene in step 1a, methylamine in step 1b and cyclobutylcarbonyl chloride in step 1c. MS: M+H⁺304.

Examples 5–7

The following chart shows the structure of compounds made according to the description in Examples 5–7 described below:

| Example | X   | R¹   | R²      | R³    |
|---------|-----|------|---------|-------|
| 5       | CH₂ | —Me  | —H      | -m-Cl |
| 6       | CH₂ | —Ph  | —Ph     | -p-Ph |
| 7       | O   | —Me  | —CH₂CH₃ | -p-Ph |

Example 5

1-(3-Chloro-phenyl)-3-(2-methylsulfanyl-cyclopentyl)-urea a) 2-Methylsulfanyl-cyclopentylamine. A solution of 1-chloro-2-methylsulfanyl-cyclopentane (314 mg, 2 mmol) in aqueous ammonia (5 mL) is added triethylamine (200 mg, 2 mmol). The resulting mixture is stirred at 100° C. for two hours, cooled and then the solvent is removed under reduced pressure. The residue is dissolved in ethyl acetate and the organic phase is washed with 5% aqueous NaHCO₃, brine, dried (Na₂SO₄) and then concentrated to an oil under reduced pressure. The crude product is used in the next step without further purification.

b) 1-(3-Chloro-phenyl)-3-(2-methylsulfanyl-cyclopentyl)-urea. To a solution of 2-methylsulfanyl-cyclopentylamine (131 mg, 1 mmol) in dichloromethane (5 mL) is added triethylamine (100 mg, 1 mmol) followed by meta-chlorophenyl isocyanate (185 mg, 1.2 mmol). The resulting mixture is stirred at room temperature overnight and then the mixture is partitioned between ethyl acetate and 5% aqueous NaHCO₃. The organic phase is washed with brine, dried (Na₂SO₄) and then concentrated to an oil under reduced pressure. The crude material is purified by chromatography on silica gel (hexane/EtOAc) to provide the target product. MS: M+H⁺285.

Example 6

1-Benzyl-3-biphenyl-4-yl-1-(2-phenylsulfanyl-cyclopentyl)-urea

Example 6 is prepared from (2-chloro-cyclopentylsulfanyl)-benzene (Example 1a) according to the procedure described for Example 5 using benzylamine in step 5a and biphenylcarbonyl isocyanate in step 5b. MS: M+H⁺479.

Example 7

3-Biphenyl-4-yl-1-(4-methylsulfanyl-tetrahydro-furan-3-yl)-1-propyl-urea a) 3-Chloro-4-phenylsulfanyl-tetrahydro-furan. 2,5-Dihydro-furan (3.50 g, 50 mmol) is added dropwise at to a solution of dimethylsulfide (3.11 g, 50 mmol) thionyl chloride (4.95 g, 50 mmol) and dimethylsulfoxide (3.91 g, 50 mmol) in acetonitrile (100 mL) cooled to −20° C. The resulting mixture is stirred at room temperature overnight and then at 70° C. for two hours. The solvent is removed under reduced pressure and the mixture is partitioned between ethyl acetate and 5% aqueous NaHCO₃. The organic extracts are washed with brine, dried (Na₂SO₄) and then concentrated to an oil under reduced pressure. The crude material is purified by chromatography on silica gel (hexane/EtOAc) to provide the desired product.

b) (4-Phenylsulfanyl-tetrahydro-furan-3-yl)-propyl-amine. To a solution of 3-chloro-4-phenylsulfanyl-tetrahydro-furan (429 mg, 2 mmol) in tetrahydrofuran (5 mL) is added triethylamine (200 mg, 2 mmol) and propylamine (293 mg, 4 mmol). The resulting mixture is stirred at 100° C. for two hours, cooled and then the solvent is removed under reduced pressure. The residue is dissolved in ethyl acetate and the organic phase is washed with 5% aqueous NaHCO$_3$, brine, dried (Na$_2$SO$_4$) and then concentrated to an oil under reduced pressure. The crude product is used in the next step without further purification.

c) 3-Biphenyl-4-yl-1-(4-methylsulfanyl-tetrahydro-furan-3-yl)-1-propyl-urea. To a solution of 4-phenylsulfanyl-tetrahydro-furan-3-yl)-propyl-amine (237 mg, 1 mmol) in dichloromethane (5 mL) is added triethylamine (100 mg, 1 mmol) followed by 4-biphenyl isocyanate (234 mg, 1.2 mmol). The resulting mixture is stirred at room temperature overnight and then the mixture is partitioned between ethyl acetate and 5% aqueous NaHCO$_3$. The organic phase is washed with brine, dried (Na$_2$SO$_4$) and then concentrated to an oil under reduced pressure. The crude material is purified by chromatography on silica gel (hexane/EtOAc) to provide the target product. MS: M+H$^+$371.

Example 8

Gene Modulating Activity of Therapeutic Agents in Colon Cancer Cells

HT29 cells are grown to a density of 10$^5$ cells/cm$^2$ in Leibovitz's L-15 medium supplemented with 2 mM L-glutamine (90%) and 10% fetal bovine serum. The cells are collected after treatment with 0.25% trypsin, 0.02% EDTA at 37° C. for 2 to 5 minutes. The trypsinized cells are then diluted with 30 ml growth medium and plated at a density of 50,000 cells per well in a 96 well plate (200 μl/well). The following day, cells are treated with either compound buffer alone, or compound buffer containing a chemical agent to be tested, for 24 hours. The media is then removed, the cells lysed and the RNA recovered using the RNAeasy reagents and protocol obtained from Qiagen. RNA is quantitated and 10 ng of sample in 1 μl are added to 24 μl of Taqman reaction mix containing 1×PCR buffer, RNAsin, reverse transcriptase, nucleoside triphosphates, amplitaq gold, tween 20, glycerol, bovine serum albumin (BSA) and specific PCR primers and probes for a reference gene (18S RNA) and a test gene, such as one that is up-regulated in cancer. Reverse transcription is then carried out at 48° C. for 30 minutes. The sample is then applied to a Perlin Elmer 7700 sequence detector and heat denatured for 10 minutes at 95° C. Amplification is performed through 40 cycles using 15 seconds annealing at 60° C. followed by a 60 second extension at 72° C. and 30 second denaturation at 95° C. Data files are then captured and the data analyzed with the appropriate baseline windows and thresholds.

For testing of the effects of a compound of Table 1, each compound was present at a concentration of 10 μM in the culture medium.

The quantitative difference between the target and reference genes is then calculated and a relative expression value determined for all of the samples used. This procedure is then repeated for each of the target genes in a given signature, or characteristic, set and the relative expression ratios for each pair of genes is determined (i.e., a ratio of expression is determined for each target gene versus each of the other genes for which expression is measured, where each gene's absolute expression is determined relative to the reference gene for each compound, or chemical agent, to be screened). The samples are then scored and ranked according to the degree of alteration of the expression profile in the treated samples relative to the control. The overall expression of the set of genes relative to the controls, as modulated by one chemical agent relative to another, is also readily ascertained. Chemical agents having the most effect on a given gene, or set of genes, are considered the most therapeutic or anti-neoplastic, depending on the tissues being studied. The results with specific agents and the HT29 cell line are presented in Table 1. In each case, the agent was present in the cell culture at a concentration of ten micromolar.

The sets of genes, or signature sets, useful in the methods of the invention disclosed herein represent a set of genes expressed at a higher level in a cancer cell line derived from colon but not expressed at a higher level in normal colon (for example, genes 1, 2, 4–10 for the data of Table 1) or whose expression is higher in normal cells (for example, genes 3 and 11 for the data of Table 1) relative to the cancer cells. The nucleotide sequences of these genes are known but not relevant to use of the compounds disclosed herein in that it is the effect of the disclosed compounds on the pattern of gene expression that is important more than the effect on a particular gene. In carrying out the methods of the invention, it is to be expected that not all cells of a given sample of suspected cancerous cells will express all, or even most, of these genes but that a substantial expression thereof in a substantial number of such cells is sufficient to warrant a determination of a cancerous, or potentially cancerous, condition.

TABLE 1

Effects of selected compounds on expression of selected genes in HT29 cell line (a colon tumor cell line).

| Compound | Gene 1 | Gene 2 | Gene 3 | Gene 4 | Gene 5 | Gene 6 | Gene 7 | Gene 8 | Gene 9 | Gene 10 | Gene 11 |
|---|---|---|---|---|---|---|---|---|---|---|---|
| | Folds of up (+) or down (−) regulation | | | | | | | | | | |
| AV-96 | 3.5 | 2.8 | 3.2 | 2.8 | 2.8 | −4.9 | 5.3 | 2.8 | 2.5 | 1.9 | 3.7 |
| AV-221 | 64.0 | 1.4 | −3.5 | 1.4 | 1.5 | −1.1 | 90.5 | 1.6 | 1.2 | −6.5 | — |
| AV-283 | −2.1 | −1.7 | −4.6 | −1.7 | −1.5 | −3.5 | −3.7 | −1.7 | −3.7 | −3.0 | −34.3 |
| AV-916 | −2.1 | −1.1 | −8.0 | −1.3 | −1.2 | 1.0 | −1.2 | −3.0 | −6.5 | −8.6 | −3.7 |
| AV-988 | 2.6 | 2.3 | −11.3 | 1.9 | 1.9 | 2.0 | 1.2 | 1.7 | 1.3 | −4.6 | — |
| AV-1030 | 2.1 | 3.7 | −1.1 | 1.1 | 2.5 | 1.4 | −1.1 | −2.6 | −2.6 | −2.5 | −4.6 |
| AV-1241 | 1.9 | 1.7 | 29.9 | 2.0 | 1.2 | 2.8 | 26.0 | 2.1 | 9.2 | 13.0 | 27.9 |

What is claimed is:

1. A compound having a structure according to Formula (I)

wherein:
- R¹ is selected from alkyl, alkenyl, alkynyl, heteroalkyl, haloalkyl, aryl, arylalkyl, heteroaryl, heteroarylalkyl, cycloalkyl, and heterocycloalkyl;
- R² is selected from alkyl, alkenyl, alkyny, heteroalkyl, haloalkyl, arylalkyl, heteroarylalkyl, cycloalkylalkyl, and heterocycloalkylalkyl;
- R³ is selected from aryl, heteroaryl, cycloalkyl, and heterocycloalkyl;
- W is selected from CH₂, O and S;
- n is 0 to 3:
- X is selected from S or O;
- Y, if present, is selected from NH, NR, O or S, where R is selected from hydrogen, alkyl, alkenyl, alkynyl, heteroalkyl, haloalkyl, aryl, arylalkyl, heteroarylalkyl, cycloalkylalkyl, and heterocycloalkylalkyl or Y may not be present at all; and
- Z, if present, can represent a bond or is selected from lower alkyl, O or S.

Figure 1A:
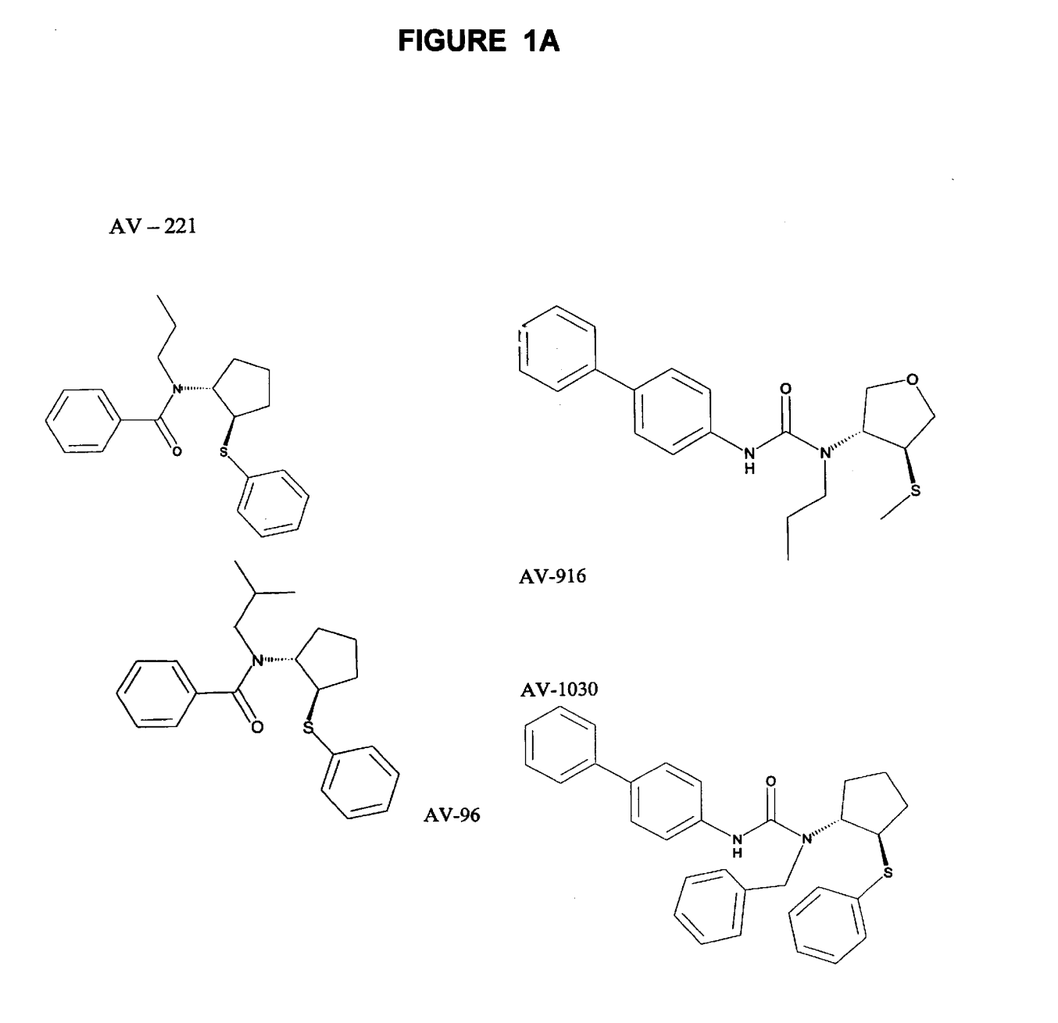
Figure 1B:
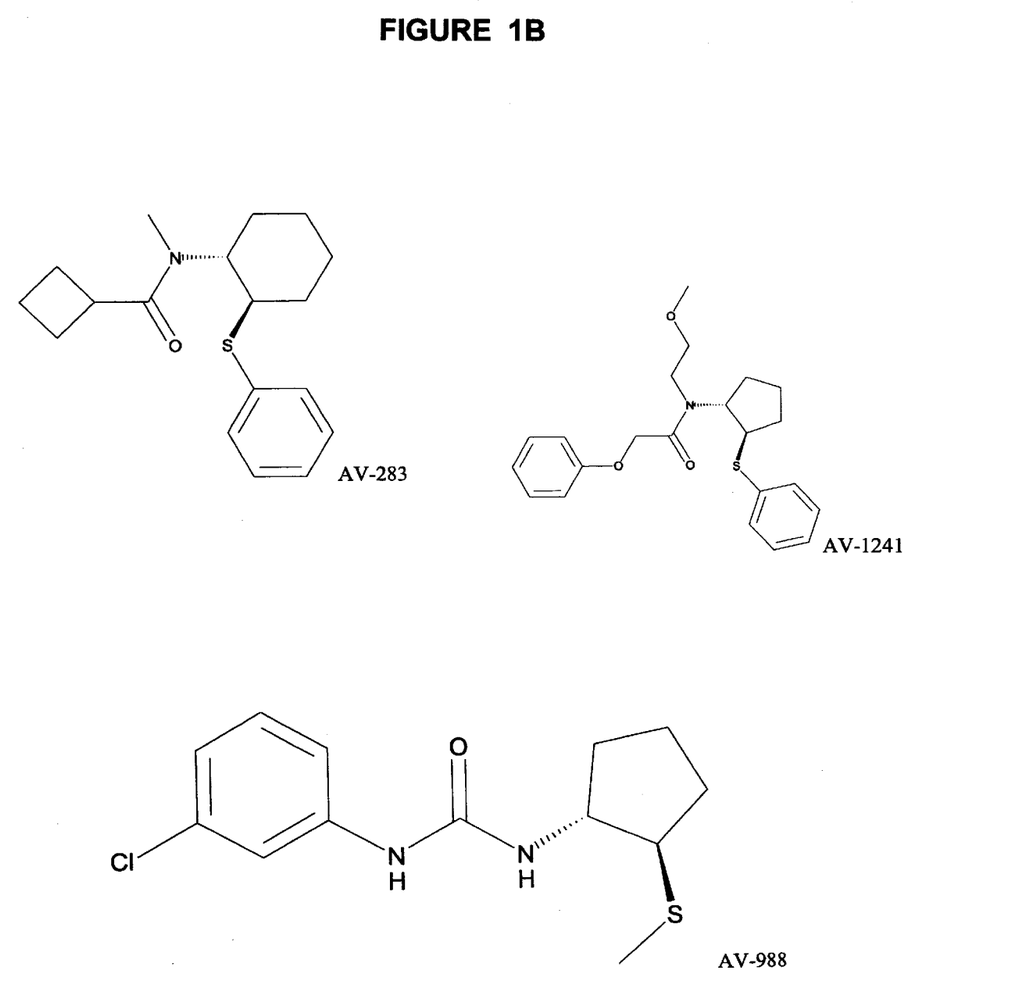

2. A compound having a structure selected from the group consisting of the structures of FIG. 1.

3. A pharmaceutical composition comprising a therapeutically effective amount of a compound of claim 1 or 2 suspended in a pharmaceutically-acceptable carrier.

4. A process for preventing or treating a disease associated with a change in levels of expression of particular sets of genes in a mammal comprising administering to said mammal an effective amount of a compound of claim 1.

5. A process for preventing or treating a disorder modulated by altered gene expression, wherein the disorder is selected from the group consisting of cancer, cardiovascular disorders, arthritis, osteoporosis, inflammation and skin disorders, by administering to a mammal in need of such treatment a safe and effective amount of a compound according to claim 1.

6. The process of claim 5, wherein the disorder is cancer, and the treatment prevents, arrests or reverts tumor growth and metastasis.

7. The process of claim 6 wherein the disorder is colon cancer.

8. The process of claim 5, wherein the disorder is a cardiovascular disorder chosen from the group consisting of dilated cardiomyopathy, congestive heart failure, atherosclerosis, plaque rupture, reperfusion injury, ischemia, chronic obstructive pulmonary disease, angioplasty restenosis, and aortic aneurysm.

9. The process of claim 5 wherein the disorder is arthritis and is selected from the group consisting of osteoarthritis and rheumatoid arthritis.

10. The process of claim 5 wherein the disorder is periodontal disease.

11. A process of claim 5 wherein said inflammatory condition is chosen from the group consisting of inflammatory bowel disease, Crohn's Disease, ulcerative colitis, pancreatitis, diverticulitis, acne inflammation, bronchitis, arthritis, asthma.

12. The process of claim 5 wherein the disorder is a skin disorder selected from the group consisting of wound healing, wrinkle repair and prevention, U.V. skin damage, epidermolysis bullosa, psoriasis, sclerodema, atopic dermatitis, and scarring.

13. A process for preventing or treating a disease associated with a change in levels of expression of particular sets of genes in a mammal comprising administering to said mammal an effective amount of a compound of claim 2.

14. A process for preventing or treating a disorder modulated by altered gene expression, wherein the disorder is selected from the group consisting of cancer, cardiovascular disorders, arthritis, osteoporosis, inflammation and skin disorders, by administering to a mammal in need of such treatment a safe and effective amount of a compound according to claim 2.

15. The process of claim 14, wherein the disorder is cancer, and the treatment prevents, arrests or reverts tumor growth and metastasis.

16. The process of claim 15 wherein the disorder is colon cancer.

* * * * *